US 8,672,923 B2

(12) United States Patent
Ladtkow et al.

(10) Patent No.: US 8,672,923 B2
(45) Date of Patent: Mar. 18, 2014

(54) AUTOMATED PROBE PLACEMENT DEVICE (75) Inventors: Casey M. Ladtkow, Westminster, CO (US); Arnold V. DeCarlo, Frederick, CO (US)

(73) Assignee: Covidien LP, Mansfield, MA (US)

(*) Notice: Subject to any disclaimer, the term of this patent is extended or adjusted under 35 U.S.C. 154(b) by 445 days.

(21) Appl. No.: 12/722,034

(22) Filed: Mar. 11, 2010

(65) Prior Publication Data
US 2011/0224504 A1   Sep. 15, 2011

(51) Int. Cl.
*A61B 17/00* (2006.01)

(52) U.S. Cl.
USPC .......................................................... 606/1

(58) Field of Classification Search
USPC .......................................................... 606/1
See application file for complete search history.

(56) References Cited

U.S. PATENT DOCUMENTS

| D263,020 S | 2/1982 | Rau, III | |
|---|---|---|---|
| 4,386,602 A | 6/1983 | Sheldon et al. | |
| 4,498,481 A * | 2/1985 | Lemke | 600/547 |
| 4,573,473 A * | 3/1986 | Hess | 600/437 |
| D295,893 S | 5/1988 | Sharkany et al. | |
| D295,894 S | 5/1988 | Sharkany et al. | |
| 5,010,892 A * | 4/1991 | Colvin et al. | 600/587 |
| 5,057,106 A | 10/1991 | Kasevich et al. | |
| 5,247,938 A | 9/1993 | Silverstein et al. | |
| 5,391,144 A | 2/1995 | Sakurai et al. | |
| RE35,880 E * | 8/1998 | Waldman et al. | 600/374 |
| 5,800,350 A | 9/1998 | Coppleson et al. | |
| 5,916,212 A | 6/1999 | Baust et al. | |
| D424,694 S | 5/2000 | Tetzlaff et al. | |
| D425,201 S | 5/2000 | Tetzlaff et al. | |
| D449,886 S | 10/2001 | Tetzlaff et al. | |
| D457,958 S | 5/2002 | Dycus et al. | |
| D457,959 S | 5/2002 | Tetzlaff et al. | |
| 6,461,037 B1 * | 10/2002 | O'Leary | 374/158 |
| 6,471,697 B1 | 10/2002 | Lesh | |
| D496,997 S | 10/2004 | Dycus et al. | |
| D499,181 S | 11/2004 | Dycus et al. | |
| 6,973,931 B1 * | 12/2005 | King | 132/212 |
| D525,361 S | 7/2006 | Hushka | |
| D531,311 S | 10/2006 | Guerra et al. | |

(Continued)

FOREIGN PATENT DOCUMENTS

| DE | 390937 | 3/1924 |
|---|---|---|
| DE | 1099658 | 2/1961 |

(Continued)

OTHER PUBLICATIONS

U.S. Appl. No. 08/483,742, filed Jun. 7, 1995.

(Continued)

*Primary Examiner* — Bill Thomson
*Assistant Examiner* — John R Downey (57) ABSTRACT A probe includes a handle and an elongated shaft with proximal and distal ends. The elongated shaft includes a plurality of axial holding tube projections to house a corresponding plurality of measurement probes. The probe further includes an actuation system to operably engage each of the plurality of measurement probes to permit selective actuation thereof. Each of the plurality of measurement probes is capable of being advanced distally relative to the handle in response to the actuation thereof. The plurality of measurement probes measure one or more parameters selected from a group consisting of temperature, physiological pressure, conductivity, aquametry, pH level, and oxygen level.

16 Claims, 7 Drawing Sheets (56) References Cited

U.S. PATENT DOCUMENTS

| | | | |
|---|---|---|---|
| D533,942 S | 12/2006 | Kerr et al. | |
| D535,027 S | 1/2007 | James et al. | |
| D541,418 S | 4/2007 | Schechter et al. | |
| D541,938 S | 5/2007 | Kerr et al | |
| 7,326,203 B2 | 2/2008 | Papineau et al. | |
| 7,331,957 B2 | 2/2008 | Woloszko et al. | |
| D564,662 S | 3/2008 | Moses et al. | |
| 7,763,018 B2 * | 7/2010 | DeCarlo et al. | 606/41 |
| 8,181,995 B2 * | 5/2012 | DeCarlo | 285/124.2 |
| 2003/0169603 A1 | 9/2003 | Luloh et al. | |
| 2006/0142755 A1 * | 6/2006 | Elliott | 606/41 |
| 2007/0049922 A1 * | 3/2007 | Rontal | 606/41 |
| 2009/0156958 A1 * | 6/2009 | Mehta et al. | 600/549 |
| 2010/0010480 A1 * | 1/2010 | Mehta et al. | 606/9 |

FOREIGN PATENT DOCUMENTS

| | | |
|---|---|---|
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2415263 | 10/1975 |
| DE | 2429021 | 1/1976 |
| DE | 2460481 | 6/1976 |
| DE | 2602517 | 7/1976 |
| DE | 2504280 | 8/1976 |
| DE | 2627679 | 1/1977 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 8712328 | 3/1988 |
| DE | 3711511 | 6/1988 |
| DE | 3904558 | 8/1990 |
| DE | 3942998 | 7/1991 |
| DE | 4238263 | 5/1993 |
| DE | 4303882 | 8/1994 |
| DE | 4339049 | 5/1995 |
| DE | 29616210 | 1/1997 |
| DE | 19608716 | 4/1997 |
| DE | 19751106 | 5/1998 |
| DE | 19717411 | 11/1998 |
| DE | 19751108 | 5/1999 |
| DE | 19801173 | 7/1999 |
| DE | 19848540 | 5/2000 |
| DE | 10224154 | 12/2003 |
| DE | 10328514 | 3/2005 |
| DE | 102004022206 | 12/2005 |
| DE | 202005015147 | 3/2006 |
| EP | 0 246 350 | 11/1987 |
| EP | 0 521 264 | 1/1993 |
| EP | 0 556 705 | 8/1993 |
| EP | 0 558 429 | 9/1993 |
| EP | 0 836 868 | 4/1998 |
| EP | 0 882 955 | 12/1998 |
| EP | 1 159 926 | 5/2001 |
| FR | 179 607 | 11/1906 |
| FR | 1 275 415 | 9/1960 |
| FR | 1 347 865 | 11/1963 |
| FR | 2 276 027 | 6/1974 |
| FR | 2 235 669 | 1/1975 |
| FR | 2 313 708 | 12/1976 |
| FR | 2 502 935 | 10/1982 |
| FR | 2 517 953 | 6/1983 |
| FR | 2 573 301 | 11/1984 |
| FR | 2 862 813 | 5/2005 |
| FR | 2 864 439 | 7/2005 |
| JP | 5-5106 | 1/1993 |
| JP | 05-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09010223 | 1/1997 |
| JP | 11244298 | 9/1999 |
| JP | 2000342599 | 12/2000 |
| JP | 2000350732 | 12/2000 |
| JP | 2001008944 | 1/2001 |
| JP | 2001029356 | 2/2001 |
| JP | 2001128990 | 5/2001 |
| JP | 2008142467 | 6/2008 |
| SU | 166452 | 11/1964 |
| SU | 401367 | 11/1974 |
| SU | 727201 | 4/1980 |

OTHER PUBLICATIONS

U.S. Appl. No. 08/136,098, filed Oct. 14, 1993.
U.S. Appl. No. 12/199,935, filed Aug. 28, 2008.
U.S. Appl. No. 12/203,474, filed Sep. 3, 2008.
U.S. Appl. No. 12/236,686, filed Sep. 24, 2008.
U.S. Appl. No. 12/244,850, filed Oct. 3, 2008.
U.S. Appl. No. 12/250,110, filed Oct. 13, 2008.
U.S. Appl. No. 12/250,171, filed Oct. 13, 2008.
U.S. Appl. No. 12/251,857, filed Oct. 15, 2008.
U.S. Appl. No. 12/253,457, filed Oct. 17, 2008.
U.S. Appl. No. 12/389,906, filed Feb. 20, 2009.
U.S. Appl. No. 12/389,915, filed Feb. 20, 2009.
U.S. Appl. No. 12/401,268, filed Mar. 10, 2009.
U.S. Appl. No. 12/416,583, filed Apr. 1, 2009.
U.S. Appl. No. 12/419,395, filed Apr. 7, 2009.
U.S. Appl. No. 12/423,609, filed Apr. 14, 2009.
U.S. Appl. No. 12/436,237, filed May 6, 2009.
U.S. Appl. No. 12/436,239, filed May 6, 2009.
U.S. Appl. No. 12/436,231, filed May 6, 2009.
U.S. Appl. No. 12/472,831, filed May 27, 2009.
U.S. Appl. No. 12/475,082, filed May 29, 2009.
U.S. Appl. No. 12/476,960, filed Jun. 2, 2009.
U.S. Appl. No. 12/487,917, filed Jun. 19, 2009.
U.S. Appl. No. 12/493,302, filed Jun. 29, 2009.
U.S. Appl. No. 12/504,738, filed Jul. 17, 2009.
U.S. Appl. No. 12/535,851, filed Aug. 5, 2009.
U.S. Appl. No. 12/535,856, filed Aug. 5, 2009.
U.S. Appl. No. 12/536,616, filed Aug. 6, 2009.
U.S. Appl. No. 12/542,348, filed Aug. 17, 2009.
U.S. Appl. No. 12/542,785, filed Aug. 18, 2009.
U.S. Appl. No. 12/547,155, filed Aug. 25, 2009.
U.S. Appl. No. 12/548,644, filed Aug. 27, 2009.
U.S. Appl. No. 12/555,576, filed Sep. 8, 2009.
U.S. Appl. No. 12/556,010, filed Sep. 9, 2009.
U.S. Appl. No. 12/561,096, filed Sep. 16, 2009.
U.S. Appl. No. 12/562,575, filed Sep. 18, 2009.
U.S. Appl. No. 12/562,842, filed Sep. 18, 2009.
U.S. Appl. No. 12/566,299, filed Sep. 24, 2009.
U.S. Appl. No. 12/568,067, filed Sep. 28, 2009.
U.S. Appl. No. 12/568,524, filed Sep. 28, 2009.
U.S. Appl. No. 12/568,551, filed Sep. 28, 2009.
U.S. Appl. No. 12/568,777, filed Sep. 29, 2009.
U.S. Appl. No. 12/568,838, filed Sep. 29, 2009.
U.S. Appl. No. 12/568,883, filed Sep. 29, 2009.
U.S. Appl. No. 12/568,972, filed Sep. 29, 2009.
U.S. Appl. No. 12/569,171, filed Sep. 29, 2009.
U.S. Appl. No. 12/569,685, filed Sep. 29, 2009.
U.S. Appl. No. 12/582,857, filed Oct. 21, 2009.
U.S. Appl. No. 12/606,769, filed Oct. 27, 2009.
U.S. Appl. No. 12/607,221, filed Oct. 28, 2009.
U.S. Appl. No. 12/607,268, filed Oct. 28, 2009.
U.S. Appl. No. 12/619,462, filed Nov. 16, 2009.
U.S. Appl. No. 12/620,289, filed Nov. 17, 2009.

(56) References Cited

OTHER PUBLICATIONS

Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok™ Breast Lesion Needle/ Wire Localizer,-Namic® Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Dumey et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure™ Device in the Hemostasis of Small, Medium, and Large-Sized Arteries" Carolinas Laparoscopic and Advanced Surgery Program, Carolinas Medical Center, Charlotte, NC 2003.
Carus et al., "Initial Experience With the LigaSure™ Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 94 In Biologic Effects of Nonionizing Electromagnetic Fields, CRC Press, Inc., pp. 1424-1428.
Chung et al., "Clinical Experience of Sutureless Closed Hemorrhoidectomy with LigaSure™" Diseases of the Colon & Rectum, vol. 46, No. 1, Jan. 2003.
Cosman et al., "Methods of Making Nervous System Lesions" In William RH, Rengachary SS (eds): Neurosurgery, New York: McGraw Hill, vol. 111, (1984), pp. 2490-2499.
Cosman et al., "Radiofrequency Lesion Generation and its Effect on Tissue Impedance", Applied Neurophysiology, 51:230-242, 1988.
Cosman et al., "Theoretical Aspects of Radiofrequency Lesions in the Dorsal Root Entry Zone" Neurosurgery 15:(1984), pp. 945-950.

Crawford et al., "Use of the LigaSure™ Vessel Sealing System in Urologic Cancer Surger" Grand Rounds in Urology 1999, vol. 1, Issue 4, pp. 1 0-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline, "Light Key Projection Keyboard" 2004 Advanced Input Systems, located at: <http://www.advanced-input.com/lightkey> last visited on Feb. 10, 2005.
Esterline Product Literature, "Light Key: Visualize a Virtual Keyboard. One With No Moving Parts", Nov. 1, 2003; 4 pages.
Geddes et al., "The Measurement of Physiologic Events by Electrical Impedence" Am. J. MI, Jan. Mar. 1964, pp. 16-27.
Goldberg et al., "Image-guided Radiofrequency Tumor Ablation: Challenges and Opportunities—Part I", (2001) J Vasc. Interv. Radiol, vol. 12, pp. 1021-1032.
Goldberg et al. (1995) "Saline-enhanced RF Ablation: Demonstration of Efficacy and Optimization of Parameters", Radiology, 197(P): 140 (Abstr).
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
Heniford et al., "Initial Results with an Electrothermal Bipolar Vessel Sealer" Surgical Endoscopy (2001) 15:799-801.
Herman at al., "Laparoscopic Intestinal Resection With the LigaSure™ Vessel Sealing System: A Case Report" Innovations That Work, Feb. 2002.
Humphries Jr. et al., "Finite Element Codes to Model Electrical Heating and Non LInear Thermal Transport in Biological Media", Proc. ASME HTD-355, 131 (1997).
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Jarrett et al., "Use of the LigaSure™ Vessel Sealing System for Peri-Hilar Vessels in Laparoscopic Nephrectomy" Sales/Product Literature 2000.
Johnson et al., "Evaluation of a Bipolar Electrothermal Vessel Sealing Device in Hemorrhoidectomy" Sales/Product Literature, Jan. 2004.
Johnson, "Evaluation of the LigaSure™ Vessel Sealing System in Hemorrhoidectormy" American College of Surgeons (ACS) Clinic La Congress Poster (2000).
Johnson, "Use of the LigaSure™ Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659-662, Sep. 1983.
Joseph Ortenberg, "LigaSure™ System Used in Laparoscopic 1st and 2nd Stage Orchiopexy" Innovations That Work, Nov. 2002.
K. Ogata, Modern Control Engineering, Prentice-Hall, Englewood Cliffs, N.J., 1970.
Kennedy et al., "High-burst-strength, feedback-controlled bipolar vessel sealing" Surgical Endoscopy (1998) 12: 876-878.
Kopans, D.B. et al., (Nov. 1985) "Spring Hookwire Breast Lesion Localizer: Use with Rigid-Compression. Mammographic Systems," Radiology 157(2):537-538.
Koyle et al., "Laparoscopic Palomo Varicocele Ligation in Children and Adolescents" Pediatric Endosurgery & Innovative Techniques, vol. 6, No. 1, 2002.
LigaSure™ Vessel Sealing System, the Seal of Confidence in General , Gynecologic, Urologic, and Laparaoscopic Surgery, Sales/ Product Literature, Jan. 2004.
Livraghi et al., (1995) "Saline-enhanced RF Tissue Ablation in the Treatment of Liver Metastases", Radiology, p. 140 (Abstr).

(56) References Cited

OTHER PUBLICATIONS

Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants" Medical Physics. 9(3), May/Jun. 1982.
Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" Int'l Federation of Gynecology and Obstetrics FIGO World Congress 2000, Washington, DC.
MDTECH product literature (Dec. 1999) "FlexStrand": product description, 1 page.
MDTECH product literature (Mar. 2000) I'D Wire: product description, 1 page.
Medtrex Brochure "The O.R. Pro 300" 1 page, Sep. 1998.
Michael Choti, "Abdominoperineal Resection with the LigaSure™ Vessel Sealing System and LigaSure™ Atlas 20 cm Open Instrument" Innovations That Work, Jun. 2003.
Muller et al., "Extended Left Hemicolectomy Using the LigaSure™ Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . . " Journal of Applied Sciences Yingyong Kexue Xuebao, Shangha CN, vol. 23, No. 2:(Mar. 2005); pp. 160-184.
Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/77).
P.R. Stauffer et al., "Interstitial Heating Technologies", Thermoradiotheray and Thermochemotherapy (1995) vol. I, Biology, Physiology, Physics, pp. 279-320.
Palazzo et al., "Randomized clinical trial of LigaSure™ versus open haemorrhoidectomy" British Journal of Surgery 2002,89,154-157
"Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Apr. 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSure™ Vessel Sealing System in Minimally Invasive Surgery in Children" Int'l Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001) 71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Solbiati et al. (1995) "Percutaneous US-guided RF Tissue Ablation of Liver Metastases: Long-term Follow-up", Radiology, pp. 195-203.
Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Stuart W. Young, Nuclear Magnetic Resonance Imaging—Basic Principles, Raven Press, New York, 1984.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817-825.
Urologix, Inc.-Medical Professionals: Targis™ Technology (Date Unknown). "Overcoming the Challenge" located at: <http://www.urologix.com!medicaUtechnology.html > last visited on Apr. 27, 2001, 3 pages.
Urrutia et al., (1988). "Retractable-Barb Needle for Breast Lesion Localization: Use in 60 Cases," Radiology 169(3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation—'COA-COMP'" Neurosurgical Review 7:2-3 (1984) pp. 187-190.
W. Scott Helton, "LigaSure™ Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
European Search Report EP 98300964.8 dated Dec. 13, 2000.
European Search Report EP 98944778 dated Nov. 7, 2000.
European Search Report EP 98958575.7 dated Oct. 29, 2002.
European Search Report EP 03721482 dated Feb. 6, 2006.
European Search Report EP 04009964 dated Jul. 28, 2004.
European Search Report EP 04013772 dated Apr. 11, 2005.
European Search Report EP 04015980 dated Nov. 3, 2004.
European Search Report EP 04015981.6 dated Oct. 25, 2004.
European Search Report EP 04027314 dated Mar. 31, 2005.
European Search Report EP 04027479 dated Mar. 17, 2005.
European Search Report EP 04027705 dated Feb. 10, 2005.
European Search Report EP 04710258 dated Oct. 15, 2004.
European Search Report EP 04752343.6 dated Jul. 31, 2007.
European Search Report EP 04778192.7 dated Jul. 1, 2009.
European Search Report EP 05002027.0 dated May 12, 2005.
European Search Report EP 05002769.7 dated Jun. 19, 2006.
European Search Report EP 05013463.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.
European Search Report EP 05021025.1 dated Mar. 13, 2006.
European Search Report EP 05021197.8 dated Feb. 20, 2006.

(56) References Cited

OTHER PUBLICATIONS

European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report EP 05025423.4 dated Jan. 19, 2007.
European Search Report EP 05025424 dated Jan. 30, 2007.
European Search Report EP 05810523 dated Jan. 29, 2009.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Jul. 25, 2006.
European Search Report EP 06008779.8 dated Jul. 13, 2006.
European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 06019768 dated Jan. 17, 2007.
European Search Report EP 06020574.7 dated Oct. 2, 2007.
European Search Report EP 06020583.8 dated Feb. 7, 2007.
European Search Report EP 06020584.6 dated Feb. 1, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
European Search Report EP 07000885.9 dated May 15, 2007.
European Search Report EP 07001480.8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.
European Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2007.
European Search Report EP 07015601.3 dated Jan. 4, 2007.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report EP 07019178.8 dated Feb. 12, 2008.
European Search Report EP 07020283.3 dated Feb. 5, 2008.
European Search Report EP 07253835.8 dated Dec. 20, 2007.
European Search Report EP 08001019 dated Sep. 23, 2008.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
European Search Report EP 08011282 dated Aug. 14, 2009.
European Search Report EP 08011705 dated Aug. 20, 2009.
European Search Report EP 08011705.4 extended dated Nov. 4, 2009.
European Search Report EP 08012829.1 dated Oct. 29, 2008.
European Search Report EP 08015842 dated Dec. 5, 2008.
European Search Report EP 08019920.1 dated Mar. 27, 2009.
European Search Report EP 08169973.8 dated Apr. 6, 2009.
European Search Report EP 09010873.9 extended dated Nov. 13, 2009.
European Search Report EP 09010877.0 extended dated Dec. 3, 2009.
European Search Report EP 09156861.8 dated Aug. 4, 2009.
European Search Report EP 09161502.1 dated Sep. 2, 2009.
European Search Report EP 09161502.1 extended dated Oct. 30, 2009.
European Search Report EP 09166708 dated Oct. 15, 2009.
European Search Report EP 09169376.2 extended dated Dec. 16, 2009.
European Search Report EP 09172838.6 extended dated Jan. 20, 2010.
European Search Report EP 09173268.5 extended dated Jan. 27, 2010.
International Search Report PCT/US98/18640 dated Jan. 29, 1998.
International Search Report PCT/US98/23950 dated Jan. 14, 1998.
International Search Report PCT/US99/24869 dated Feb. 11, 2000.
International Search Report PCT/US01/11218 dated Aug. 14, 2001.
International Search Report PCT/US01/11224 dated Nov. 13, 2001.
International Search Report PCT/US01/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.
International Search Report PCT/US03/22900 dated Dec. 2, 2003.
International Search Report PCT/US03/37110 dated Jul. 25, 2005.
International Search Report PCT/US03/37111 dated Jul. 28, 2004.
International Search Report PCT/US03/37310 dated Aug. 13, 2004.
International Search Report PCT/US04/04685 dated Aug. 27, 2004.
International Search Report PCT/US04/13273 dated Dec. 15, 2004.
International Search Report PCT/US04/15311 dated Jan. 12, 2004.
International Search Report PCT/US05/36168 dated Aug. 28, 2006.
International Search Report PCT/US08/052460 dated Apr. 24, 2008.
International Search Report PCT/US09/31658 dated Mar. 11, 2009.

* cited by examiner

AUTOMATED PROBE PLACEMENT DEVICE

BACKGROUND

1. Technical Field

The present disclosure relates to an automated placement probe and method to measure, monitor, and assess efficacy of a body cavity. In particular, the present disclosure relates to the design and use of a multi-measurement probe for providing multiple, and not necessarily complementary functions, such as measuring in-vivo activity of human or animal body tissues.

2. Background of Related Art

This present disclosure relates to instruments and methods for ablation monitoring. More particularly, the present disclosure relates to probes and methods for measuring and accessing efficacy of a body cavity.

Conventional surgical procedures involve cutting through bodily structures to expose a lesion or organ within the body for treatment. Because these procedures create considerable trauma to the patient, physicians have developed minimally invasive procedures using probes inserted into the body through body orifices or through small holes to treat or measure structures within the body. For example, the devices commonly referred to as endoscopes include an elongated body having a distal end and a proximal end. The distal end of the probe body can be inserted into the gastrointestinal tract through a body orifice. The endoscope may be equipped with optical devices such as cameras or fiber optics to permit observation of the tissues surrounding the distal end, and surgery may be performed by inserting and maneuvering surgical instruments through a channel in the endoscope body. Other probes commonly referred to as laparoscopes and orthoscopes are inserted into the body through small holes formed in surrounding tissues to reach the bodily structures to be treated or measured. Still other probes commonly referred to as catheters, can be advanced through the vascular system, as through a vein or artery, or through other bodily passages such as the urinary tract.

Typically, many of the above-described techniques require the surgeon to insert different instruments through the working lumen of the endoscope to treat tissue, separate vessels or perform other surgical procedures. Moreover, typical practice in ablation monitoring uses diagnostic imaging that is performed after a procedure is completed to assess efficacy. The ablation monitoring process uses, for example, temperature probes that are integrated into a probe or separate from the probe to gather additional information. However, these probes measure only one particular type of parameter such as temperature. If another parameter is required, the surgeon would use another type of probe. The need for careful and precise control over the probe is critical when monitoring and measuring the body cavity at the same treatment site. Additionally, multiple insertions of different probes require additional body orifices or small holes to treat or measure structures within the body. As can be appreciated, this simply adds to the overall complexity of the operation since it requires the repeated exchange of probes to measure the different data associated with a given surgical procedure.

SUMMARY

In general, it is an object of the present invention to provide a probe to measure and/or assess efficacy of a body cavity. The probe for measuring and assessing efficacy of a body cavity includes a handle and an elongated shaft with proximal and distal ends. The elongated shaft includes a plurality of axial holding tube projections to house a corresponding plurality of measurement probes. The probe further includes an actuation system to operably engage each of the plurality of measurement probes to permit selective actuation thereof to monitor and assess efficacy of a body cavity. Each of the plurality of measurement probes advances distally relative to the handle in response to actuation thereof.

In one embodiment, the plurality of measurement probes is arranged in an array-like manner within the elongated shaft. In another embodiment, the measurement probe is selected from a group consisting of temperature, physiological pressure, conductivity, aquametry, pH level, and oxygen level.

In yet another embodiment, the actuation system includes a resilient member, such as a spring removably disposed on a proximal end of each of the axial holding tube projections. The actuation system further includes at least one projecting edge coupled to a surface of the handle. The at least one projecting edge engages with a corresponding proximal end of one of the plurality of axial holding tube projections. The at least one projecting edge enables a respective plurality of axial holding tube projections to advance distally relative to the handle in response to the actuation.

In yet another embodiment, the handle of the probe is rotatable so the surgeon can selectively actuate one type of measurement probe (e.g., temperature). The probe includes an indicator number that reflects the type of measurement probe being actuated.

In yet another embodiment, the probe is able to actuate at least two measurement probes simultaneously to measure and/or assess efficacy of the treatment site.

In yet another embodiment, the operating portions are configured to deploy the plurality of measurement probes into the body cavity from first, second, and at least third positions. The first position is the plurality of measurement probes being completely inside the elongated shaft, the second position is the plurality of measurement probes being fully extended beyond the distal end of the elongated shaft, and the at least third position is the plurality of measurement probes being extended in-between the first and second positions.

These and other objects will be more clearly illustrated below by the description of the drawings and the detailed description of the preferred embodiments.

BRIEF DESCRIPTION OF THE DRAWINGS

The accompanying drawings, which are incorporated in and constitute a part of this specification, illustrate embodiments of the invention, and together with a general description of the invention given above, and the detailed description of the embodiments given below, serve to explain the principles of the invention.

DETAILED DESCRIPTION

Particular embodiments of the presently disclosed probe are described in detail with reference to the drawing figures wherein like reference numerals identify similar or identical elements.

As used herein, the term "distal" refers to that portion which is further from the user while the term "proximal" refers to that portion which is closer to the user or surgeon.

Various medical conditions, diseases and dysfunctions may be treated by ablation, using various ablation devices and techniques. Ablation is generally carried out to kill or destroy tissue at the site of treatment to bring about an improvement in medical condition being treated. In order to monitor the ablation treatment site, diagnostic imaging is typically performed after a medical procedure to assess efficacy. Moreover, various probes are used to gather medical data that requires multiple insertions into the treatment site.

As will be further described below in detail, a probe and method are disclosed to provide for the automatic deployment of multiple measurement probes. The probe enables a trocar to perform a combination of multiple functions, enabling the performance of complete procedures for ancillary or essential analytical procedures, diagnostic procedures, quantitative and qualitative analysis, operational environmental determinations, and any other task or information providing mechanism that provides information useful to the operation procedure. For example, the probe according to an embodiment of the present disclosure measures various information or parameters, such as temperature, physiological pressure, conductivity, aquametry, pH level, and oxygen level. Advantageously, the probe is easily deployed and ensures that multiple and repeated measurements are taken at the same treatment site for one point of entry into the body cavity.

Figure 1:
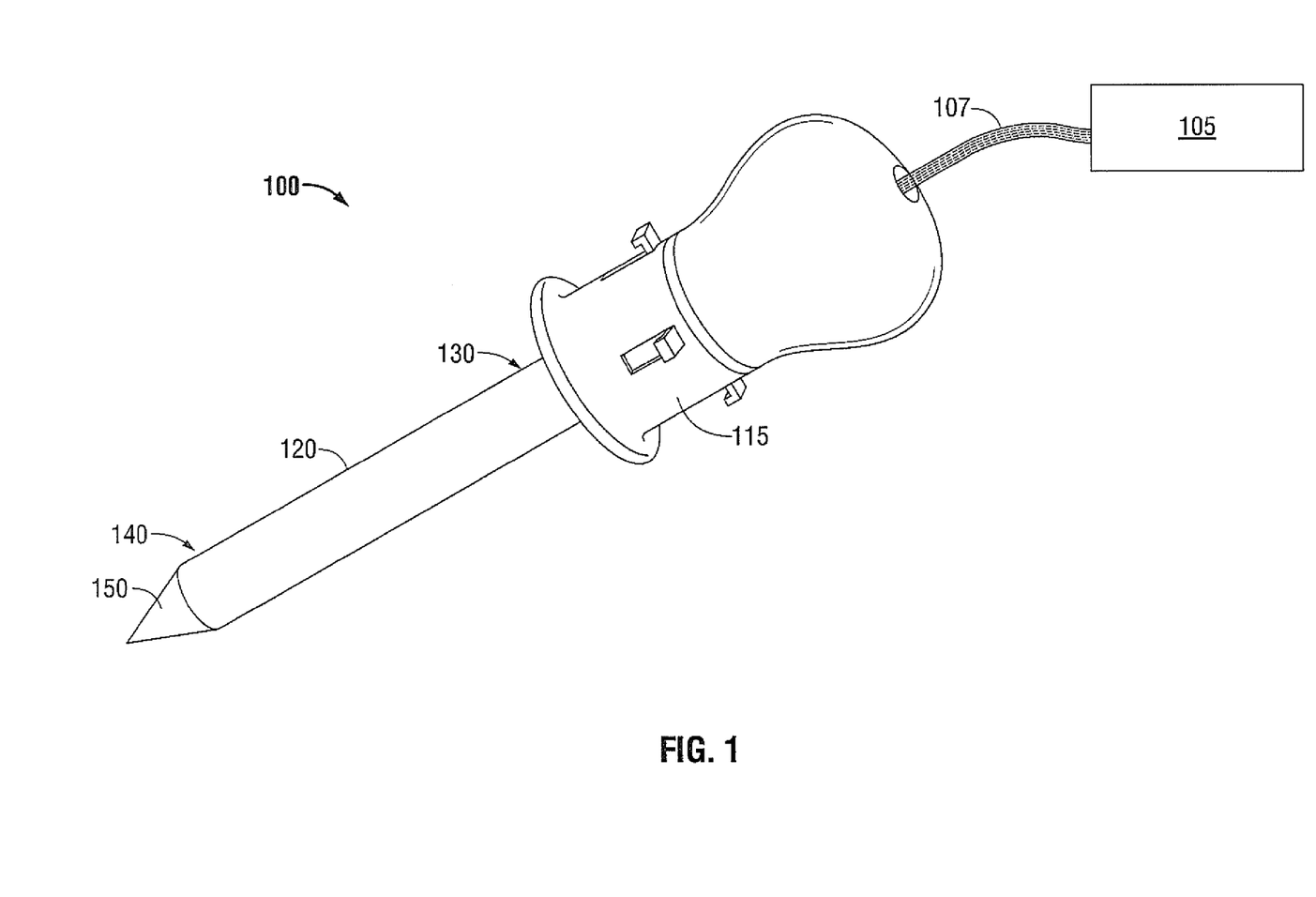
FIG. 1 is a perspective view of a probe according to an embodiment of the present disclosure.
Figure 2:
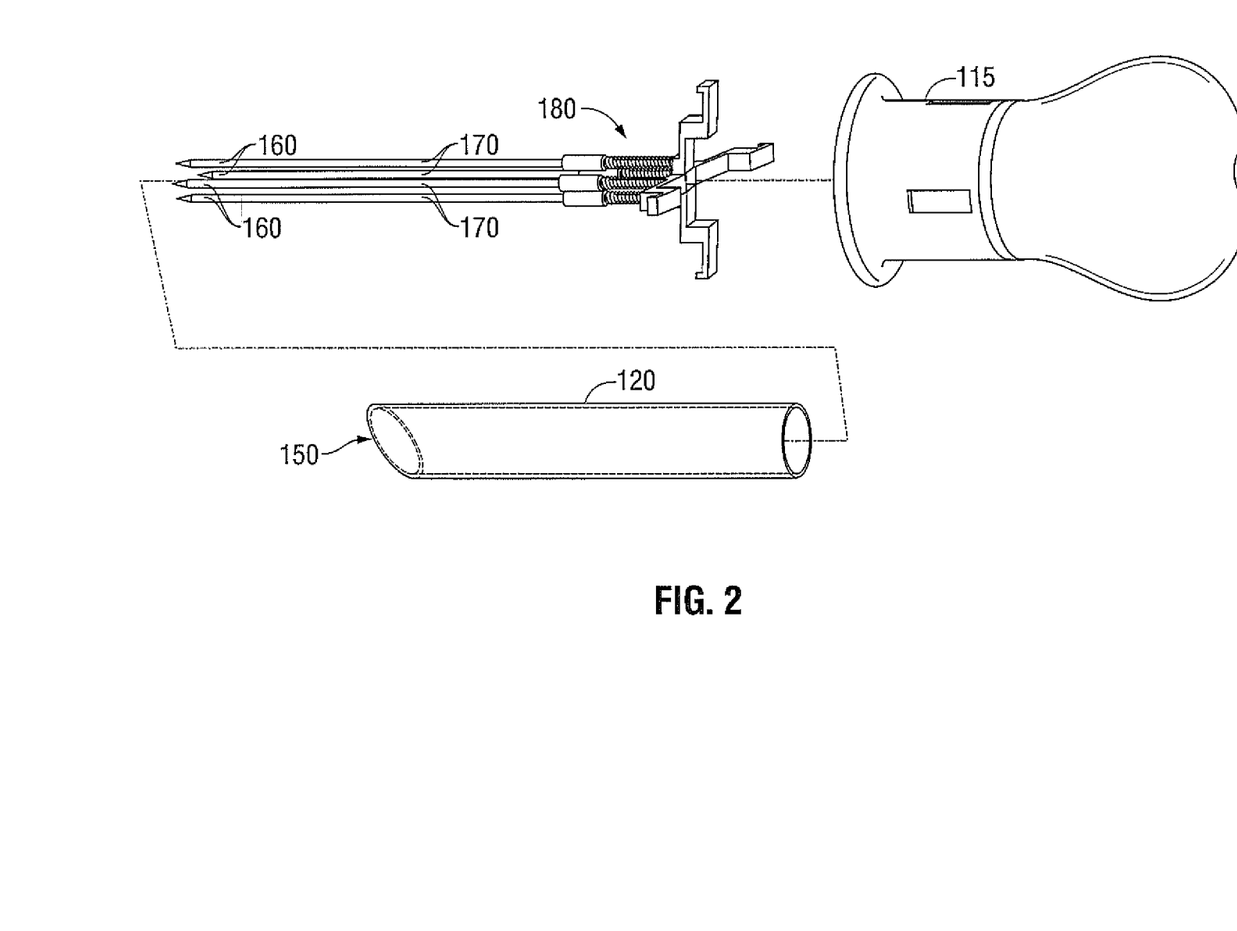
FIG. 2 is an exploded, perspective view of the probe of FIG. 1 according to an embodiment of the present disclosure.

FIGS. 1 and 2 (an exploded perspective view of the probe 100 of FIG. 1) show a probe 100 configured to measure and/or assess efficacy of a body cavity. The probe 100 includes a handle 115 and an elongated shaft 120 with proximal and distal ends 130, 140, respectively. A pointed end 150 for piercing a body tissue is disposed at a distal end of the probe 100. The elongated shaft 120 includes axial holding tube projections 160 that are configured to house a corresponding measurement probe 170. The probe 100 further includes an actuation system 180 configured to engage the measurement probes 170 and to actuate each measurement probe 170 to monitor and assess efficacy of a body cavity. Each measurement probe 170 advances distally relative to the handle 115 in response to actuation of the actuation system 180. The measurement probe(s) 170 may be configured for in-vivo measurement of human or animal body tissue. The measurement probe(s) 170 is capable of measuring and obtaining one or more parameters selected from a group consisting of: temperature, blood, physiological pressure, conductivity, aquametry, pH level, and oxygen level. For example, the blood parameter includes pH, $pO_2$ or $pCO_2$.

In one embodiment, the measurement probe(s) 170 is a fiber optic measurement probe(s). Optical measurement probe(s) 170 has the advantage of operating without taking samples, enable the simultaneous determination of the concentrations of analytes and can also be employed in unfavorable milieus (toxic, corrosive, radioactive, at risk of explosion, sterile, contaminated). Optical measurement probe(s) 170 is generally a fiber-optic element including a distal end with a light entrance opening (not shown) arranged in the axial holding tube projection(s) 160, i.e., proximate the analytes or in direct contact therewith. The probe(s) 170 is used to carry out measurements of the treatment site with the aid of a light source (not shown).

The probe 100 is connected to accessory equipment 105 via a cable 107. The accessory equipment 105 includes one or more sensors that are configured to measure, locate, orient or "index" the various measurement probes 170 disposed within the axial holding tube projections 160 of the elongated shaft 120. For example, one of the measurement probes 170 measures temperature of the treatment site and includes a sensor or an indexing tool (or other visual indicator) that cooperates with the temperature probe.

Figure 3A:
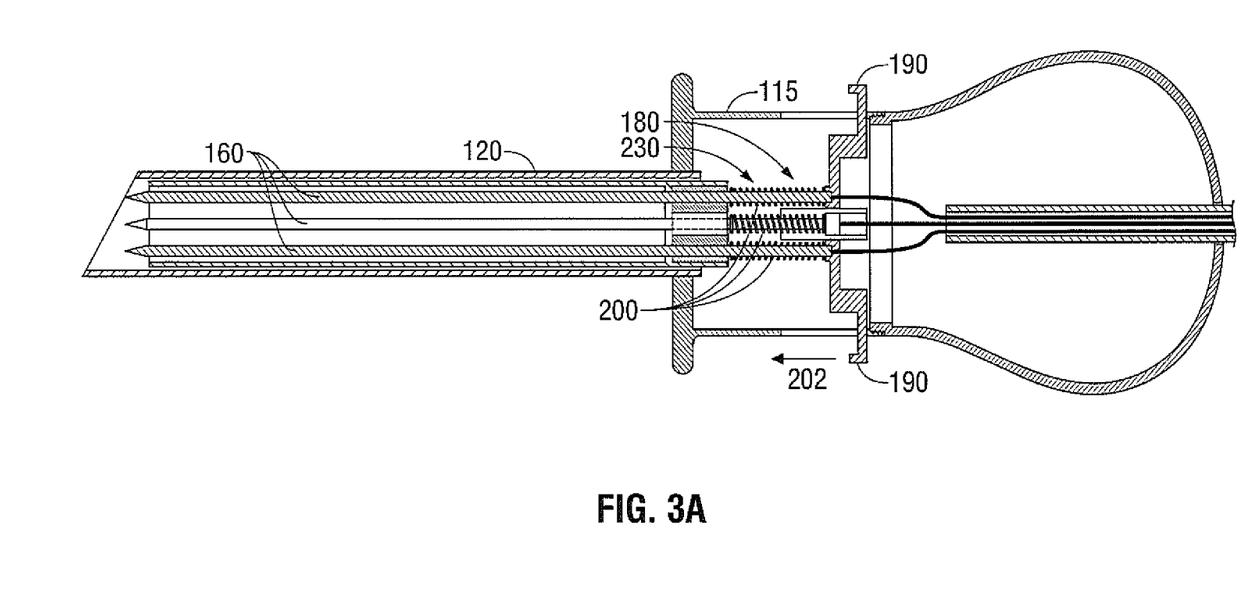
FIGS. 3A-3B are schematically-illustrated, internal views of the probe according to an embodiment of the present disclosure.
Figure 3B:
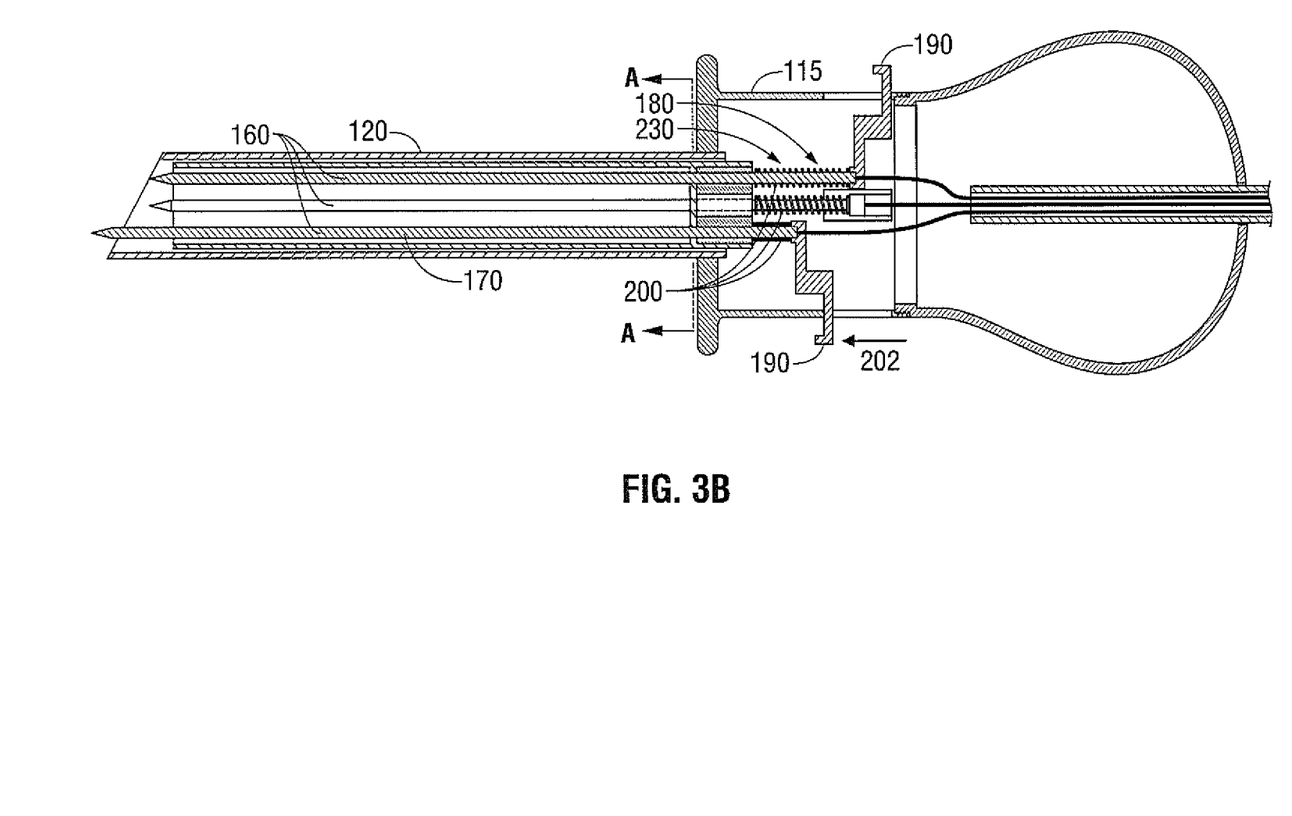

FIGS. 3A-3B are schematically-illustrated, internal views of the probe 100 and actuation system 180. The actuation system 180 enables the probe 100 to automatically retract, thereby resulting in decreased placement time and increased placement accuracy into the body cavity. As shown in FIG. 3A, the actuation system 180 includes one or more resilient members 200, such as springs, removably disposed on a proximal end 230 of each axial holding tube projection 160. The actuation system 180 further includes an operating portion (or projecting edge) 190 coupled to each axial holding tube projection 160. The operating portion 190 is engaged with one or more axial holding tube projections 160 to enable the axial holding tube projections 160 to advance distally relative to the handle 115 in response to actuation thereof.

The operating portion 190 is exposed on the outside surface of the probe handle 115 to enable the surgeon to actuate a desire measurement probe 170. Although FIG. 3A shows two (2) operating portions 190, it should be understood that there could be any suitable number of operating portions. In one particular embodiment, there are two (2) more operating portions that are placed around the circumference of the handle for a total of four (4) operating portions 190. It should further be understood that for each measurement probe 170, there is one corresponding operating portion 190. However, one operating portion 190 may be capable of actuating two or more measurement probes 170. Further, each operation portion 190 may have an indicator number to indicate the type of measurement probe (e.g., temperature, physiological pressure, conductivity, aquametry, pH level, and oxygen level.) The indicator number may include colors, labels, surface roughness, or have various shapes. For example, the indicator number may have a color on the surface of the operating portion 190 so that a user/surgeon can easily discriminate the different measurement probes.

In operation, the probe 100 may include four measurement probes 170, e.g., temperature, pH, pressure, and oxygen level. After surgery, a surgeon may want to obtain medical data from a specific treatment site. Instead of utilizing four different probes (one for each parameter) and trying to maneuver the respective probe to the same treatment site, the surgeon is able to use probe 100 to obtain all four parameters from the same treatment site in one single placement. To this end, the surgeon clicks or actuates one of the measurement probes 170 by sliding the operating portion 190 in the direction labeled as 202, as illustrated in FIG. 3A. By sliding the operating portion 190, a corresponding measurement probe (e.g., temperature) advances distally relative to the handle 115, as illustrated in FIG. 3B. The tip of the temperature probe, now in a deployed state, is capable of obtaining the temperature of the treatment site. Once the temperature data is obtained, the surgeon slides the operating portion 190 back to the original position (non-deployed state) where the tip of the temperature probe is now fully retracted inside the elongated shaft 120. The surgeon may repeat the same steps but for a different measurement probe (e.g., oxygen level).

When the measurement probe(s) 170 is deployed, the actuation system 180 may include a lockout mechanism (not shown) that enables the measurement probe(s) 170 to remain in a fully deployed state until the surgeon moves the measurement probe(s) 170 back to the non-deployed state. In another embodiment, the actuation system 180 is able to automatically deploy one or more measurement probes 170 simultaneously and then also automatically retract the measurement probes 170 simultaneously to a non-deployed state. In another embodiment, there may be a third state of deploying the measurement probe(s) 170; the third state (or intermediate position) of deployment being between the non-deployed state and deployed state.

Figure 4A:
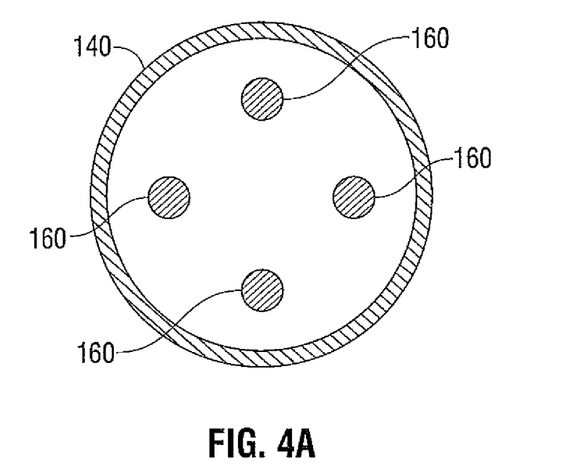
FIGS. 4A-4B are side sectional views taken along sectional lines A-A in FIG. 3B according to an embodiment of the present disclosure.
Figure 4B:
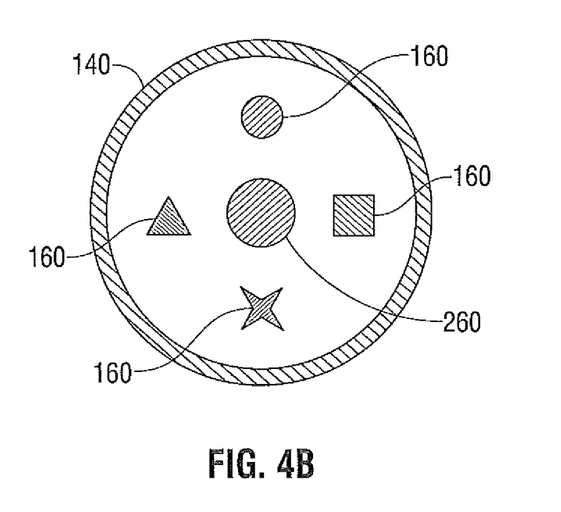

FIGS. 4A-4B are side sectional views taken along sectional lines A-A of FIG. 3B. Referring to FIG. 4A, the measurement probe(s) 170 via the axial holding tube projection(s) 160 is arranged in an array-like manner within the elongated shaft 120. In another embodiment, as illustrated in FIG. 4B, the elongated shaft 120 may include a working channel 260 disposed in the center of the elongated shaft 120 and is surrounded by the axial holding tube projection(s) 160. The working channel 260 allows for various surgical instruments to be deployed by the surgeon. The surgical instrument may include vessel sealers, coagulators, biopsy instruments, needles, probes, sensors, graspers, forceps, knives, scissors, sutures, balloon dissectors, stents, irrigators, suction devices, stabilizers, blunt dissectors, lasers, optical devices, implants and anchors. FIG. 4B also illustrates that the axial holding tube projection(s) 160 may be of any suitable shape to accommodate the various measurement probes 170. For example, the holding tube projection(s) 160 may take the shape of a square, circle, oval, rectangle, or an "X" shape.

Figure 5A:
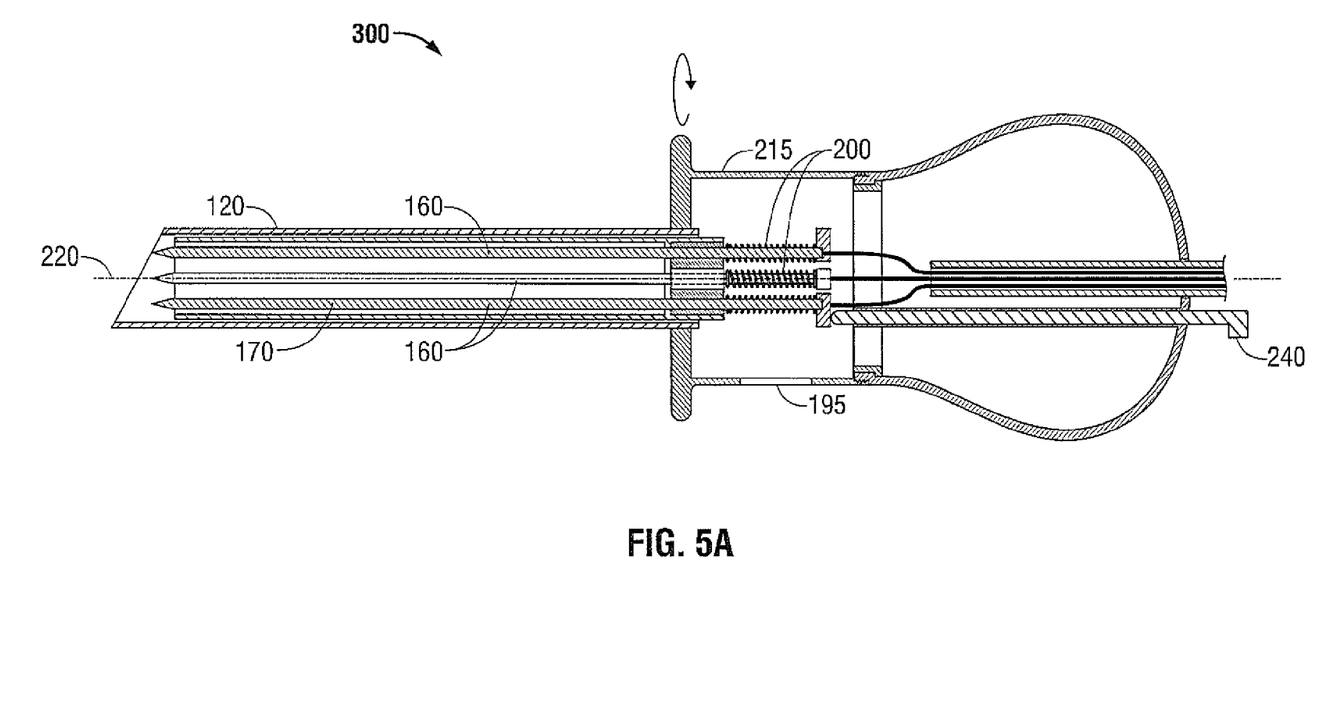
FIGS. 5A-5B are schematically-illustrated, internal views of a probe according to an embodiment of the present disclosure.
Figure 5B:
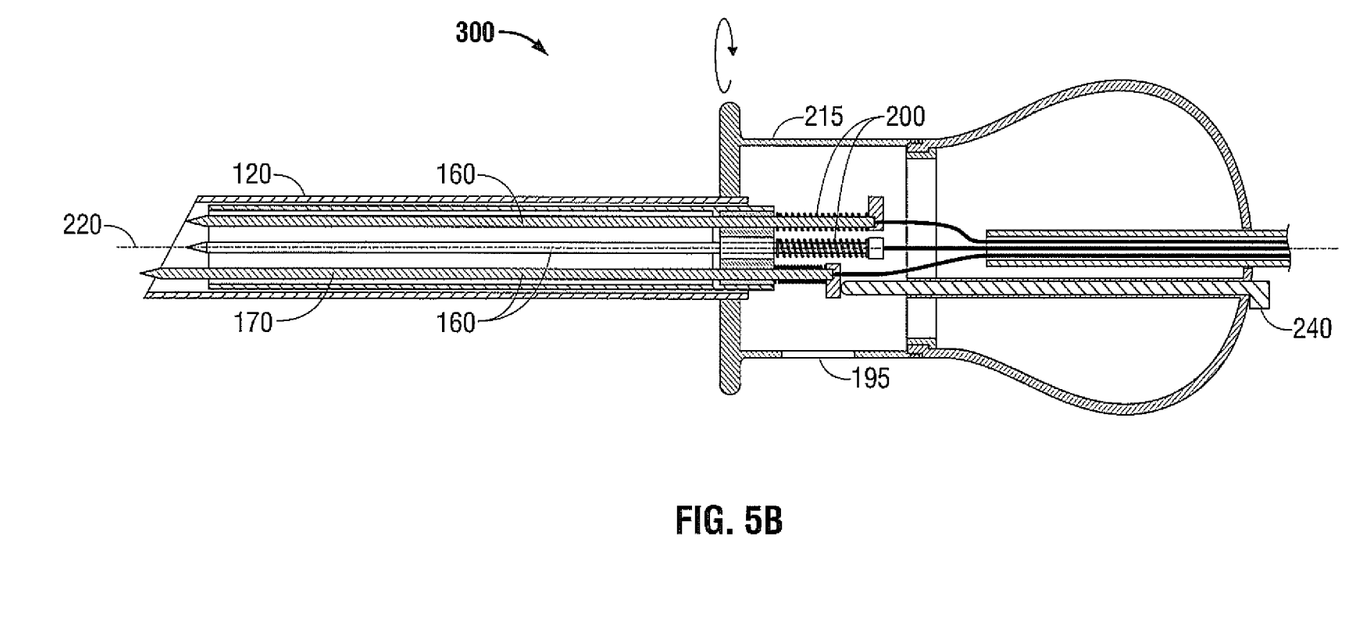

FIGS. 5A-5B are schematically-illustrated, internal views of a probe 300 according to other embodiments of the present disclosure. Probe 300 has similar working parts as probe 100 with some differences. The handle 215 of probe 300 is rotatable around a longitudinal axis 220 of the elongated shaft 120. A user deploys one of the measurement probes 170 by actuating a single operating portion 240. The single operating portion 240 is engaged with a proximal end of one of the axial holding tube projections 160. In operation, the surgeon rotates the handle 215 to a desired measurement probe 170 and then actuates the operating portion 240 as illustrated in FIG. 5B. As the handle 215 rotates, the operating portion 240 also rotates until the surgeon selects the desired measurement probe 170.

The handle 215 includes an indicator 195 to indicate a type of the plurality of measurement probe(s) 170 being actuated in the body cavity. The indicator 195 may be made of a transparent material and a user may visually distinguish the measurement probe(s) 170 by the various colors of the axial holding tube projection(s) 160 or the measurement probe(s) 170.

It should also be understood that various alternatives and modifications could be devised by those skilled in the art. The present disclosure is intended to embrace all such alternatives, modifications and variances that fall within the scope of the appended claims.

The invention claimed is:

1. A body cavity probe comprising:
a handle;
an elongated shaft with proximal and distal ends, the elongated shaft including a plurality of axial holding tube projections housing a corresponding plurality of measurement probes;
a resilient member removably disposed on a proximal end of each of the axial holding tube projections and configured to bias each of the axial tube projections proximally to a retracted configuration; and
an actuation system including an operating portion disposed on the handle and rotatable about the elongated shaft, the operating portion translatable along a longitudinal axis defined through the elongated shaft and alignable with each of the axial holding tubes,
wherein each of the plurality of measurement probes is configured to advance distally relative to the handle in response to distal translation of the operating portion,
wherein at least one of the plurality of measurement probes is configured to measure at least one parameter selected from a group consisting of temperature, physiological pressure, conductivity, aquametry, pH level, and oxygen level.

2. The body cavity probe according to claim 1, wherein at least one of the plurality of measurement probes is configured for in-vivo measurement of human or animal body tissue.

3. The body cavity probe according to claim 1, wherein at least one of the plurality of measurement probes is a fiber optic measurement probe.

4. The body cavity probe according to claim 1, wherein the plurality of measurement probes is arranged in an array within the elongated shaft.

5. The body cavity probe according to claim 1, wherein at least a portion of the operating portion is disposed on an outer surface of the handle of the probe.

6. The body cavity probe according to claim 1, wherein each of the plurality of measurement probes is actuated individually in the body cavity to measure efficacy of a surgical procedure performed within a body cavity.

7. The body cavity probe according to claim 1, wherein at least two of the plurality of measurement probes are actuated simultaneously in the body cavity to measure and assess efficacy of a body cavity.

8. The body cavity probe according to claim 1, wherein the handle includes an indicator to identify a type of the plurality of measurement probes being actuated in the body cavity.

9. The body cavity probe according to claim 1, wherein the actuation system includes:
at least one projecting edge coupled to a surface of the handle, the at least one projecting edge engages with a corresponding proximal end of one of the plurality of axial holding tube projections, the at least one projecting edge configured to enable a respective plurality of axial holding tube projections to advance distally relative to the handle in response to the actuation.

10. A method comprising the steps of:
providing a body cavity probe having:
an elongated shaft with proximal and distal ends, the elongated shaft including a plurality of axial holding tube projections that house a corresponding plurality of measurement probes;
a resilient member removably disposed on a proximal end of each of the axial holding tube projections and configured to bias each of the axial tube projections proximally to a retracted configuration; and
at least one actuator including an operating portion disposed on the handle and rotatable about the elongated shaft, the operating portion translatable along a longitudinal axis defined through the elongated shaft and alignable with each of the axial holding tubes to advance at least one of the plurality of measurement probes distally relative to the handle in response to distal translation of the operating portion; and
actuating one of the plurality of measurement probes to measure a parameter of a body cavity via the actuated measurement probe, wherein the parameter is selected from a group consisting of: temperature, physiological pressure, conductivity, aquametry, pH level, and oxygen level.

11. The method of claim 10, further including the steps of: retracting the measurement probe after the measurement; and actuating another one of the plurality of measurement probes to measure another parameter of the body cavity.

12. The method according to claim 10, wherein the plurality of measurement probes are arranged in an array-like manner within the elongated shaft.

13. The method according to claim 10, wherein each of the plurality of actuators includes a corresponding operating portion, each of the operating portion being exposed to an outer surface of the probe.

14. The method according to claim 10, wherein each of the operating portions is configured to deploy a corresponding measurement probe into the body cavity.

15. The method according to claim 10, wherein each of the plurality of measurement probes is actuated individually into the body cavity.

16. The method according to claim 10, further including the step of providing an indictor operably associated with the probe configured to indicate a type of the plurality of measurement probes being actuated into the body cavity.

* * * * *